United States Patent
Bakels et al.

(10) Patent No.: US 6,301,507 B1
(45) Date of Patent: Oct. 9, 2001

(54) MEDICAL ELECTRICAL LEAD HAVING PRE-FORMED ATRIAL SECTION

(75) Inventors: Arnoldus Bakels, Simpelveld; Nicolaas Lokhoff, Kerkrade, both of (NL)

(73) Assignee: MedTronic, Inc, Minneapolis, MN (US)

( * ) Notice: Subject to any disclaimer, the term of this patent is extended or adjusted under 35 U.S.C. 154(b) by 0 days.

(21) Appl. No.: 09/487,788

(22) Filed: Jan. 20, 2000

(51) Int. Cl.$^7$ .................................................. A61N 1/05
(52) U.S. Cl. ............................................................ 607/122
(58) Field of Search ..................................... 607/119, 122, 607/123

(56) References Cited

U.S. PATENT DOCUMENTS

| | | | |
|---|---|---|---|
| 4,154,247 | 5/1979 | O'Neill | 128/419 P |
| 4,401,126 | 8/1983 | Reenstierna | 178/784 |
| 4,627,439 | 12/1986 | Harris | 128/419 P |
| 5,628,778 | 5/1997 | Kruse et al. | 607/123 |
| 5,800,497 | 9/1998 | Bakels et al. | 607/122 |
| 5,849,032 | 12/1998 | Van Venrooij | 607/123 |
| 5,922,014 | 7/1999 | Warman et al. | 607/123 |
| 6,070,104 | 5/2000 | Hine et al. | |

*Primary Examiner*—Scott M. Getzow
(74) *Attorney, Agent, or Firm*—Thomas F. Woods; Michael J. Jaro; Harold Pattom

(57) ABSTRACT

A medical electrical lead having a pre-formed atrial portion assuming a distinctive U-shape is disclosed. The U-shaped atrial portion of the lead is configured and dimensioned to cause at least one atrial electrode disposed thereon to be pushed against the right atrial wall or right atrial sinus wall through pushing forces generated by the lead pressing against regions of the heart located near the superior vena cava or the tricuspid valve, and/or through the action of gravity. The lead provides superior coupling of the atrial electrodes thereof to the walls of the right atrium, and may be configured for single pass DDD stimulation of the right atrium and the right ventricle or other portions of the heart such as the coronary sinus or the great cardiac vein.

53 Claims, 6 Drawing Sheets

MEDICAL ELECTRICAL LEAD HAVING PRE-FORMED ATRIAL SECTION

FIELD OF THE INVENTION

The present invention relates to medical electrical leads, and methods of making, implanting and using same.

BACKGROUND OF THE INVENTION

It is well known in the field of medical electrical leads that proper coupling of stimulating electrodes to the right atrial wall is problematic, especially in respect of single pass DDD leads.

Over the years various attempts have been made to solve this problem by providing, for example, leads having positive affixation devices attached at or near the distal ends thereof such as screws, barbs and hooks, or by forming pre-formed J shapes or other configurations in the atrial portions of such leads.

See, for example, U.S. Pat. No. 4,154,247 to O'Neil for "Formable cardiac pacer lead and method of assembly and attachment to a body organ", U.S. Pat. No. 4,401,126 to Reenstierna for "Endocardial implantable lead for pacemaker" and U.S. Pat. No. 4,627,439 to Harris for "Prebent ventricular/atrial cardiac pacing lead", all of which are hereby incorporated by reference herein, each in its respective entirety. The foregoing patents all disclose single pass DDD leads having preshaped portions configured to cause the atrial electrode(s) thereof to appropriately contact and stimulate the right atrial wall.

While the leads disclosed in the foregoing patents solve some of the problems existing in the prior art respecting appropriate atrial electrode coupling in single pass leads, they produce no solution to the overriding problem, which is to provide a lead capable of providing good atrial coupling along the right atrial wall in a variety of heart shapes and sizes.

In addition to the problem of pre-formed single pass DDD leads not providing adequate electrode coupling under a variety of different physiologic conditions, there also exists the problem of implanting more than one lead in a human heart when reliable pacing of both the right atrium and right ventricle is to be carried out. In such a situation separate leads are typically implanted in the right atrium and in the right ventricle. Implanting two leads in a patient presents a challenge to the implanting physician because inserting two leads into the heart via the superior vena cava increases the surgical difficulty of the implantation procedure. Thus, while separate leads generally provide superior electrode coupling, they also present certain difficulties to the implanting physician.

The foregoing problems assume increased emphasis today owing to recent developments in heart failure treatment via pacing techniques. Effective, reliable pacing of the right atrium now assumes increased importance when treating heart failure.

Optimally pacing in heart failure includes pacing of four chambers of the heart. At a minimum, it is desirable to stimulate the left side of the heart via the intravenous route extending from the right side of the heart where synchronization of the cardiac cycle takes place via sensing of right atrial signals.

Thus, there exists a need to provide a medical electrical lead capable of solving the foregoing problems.

SUMMARY OF THE INVENTION

The present invention has certain objects. That is, the present invention provides solutions to problems existing in the prior art. Such problems include: (a) single pass DDD medical electrical leads which do not provide reliable effective coupling of the atrial electrodes thereof to the right atrial wall; (b) medical electrical leads having pre-bent or pre-curved atrial portions which do not provide good electrical coupling to the right atrial wall; (c) single pass DDD leads having atrial portions and electrodes and associated therewith that following implantation do not remain coupled to the right atrial wall; (d) medical electrical leads having a pre-formed or pre-curved atrial portions do not remain positionally or mechanically stable in respect of electrode coupling following implantation in the right atrium; and (e) medical electrical leads having atrial sections and associated electrodes which are difficult to appropriately position to permit good electrode coupling to the right atrial wall during implantation.

The present invention has certain advantages. Various embodiments of the present invention have one or more of the following advantages: (a) providing enhanced electrode coupling for stimulation of the right atrium; (b) remaining positionally and mechanically stable within the right atrium following implantation; (c) simplifying and easing implantation of a single pass DDD lead; and (d) providing a medical electrical lead which causes the atrial electrodes thereof to be pushed against the right atrial wall or right atrial sinus wall either through the action of gravity or a pushing force exerted by a pre-configured atrial section thereof.

The present invention has certain features. Various embodiments of the present invention have one or more of the following features: (a) a medical electrical lead having a substantially U-shaped atrial section having one or more atrial stimulation electrodes disposed thereon; (b) a medical electrical lead having an atrial section configured for implantation within the right atrium such that the electrode portion thereof is pushed against the right atrial wall by forces acting on the atrial section exerted by gravity or regions of heart located near the superior vena cava and/or the tricuspid valve; (c) a medical electrical lead having an atrial section comprising five distinct portions: a first proximal atrial portion; a second atrial portion; a third atrial portion; a fourth atrial portion; and a distal fifth atrial portion, where the third portion has at least one electrode disposed thereon for effecting atrial stimulation, the atrial section being geometrically configured to provide a pushing force to urge the at least one electrode against a right atrial wall or right atrial sinus wall; (d) a medical electrical lead having a pre-formed atrial section configured to cause at least one atrial electrode thereof to be pushed against a right atrial wall or right atrial sinus wall, portions of the lead disposed distally from the atrial section being configured for implantation within a right ventricle, a coronary sinus and/or a great cardiac vein of the patient's heart; (e) an elongated medical electrical lead for intra-cardiac electrical stimulation of a heart of a patient, the lead comprising a lead body extending between a proximal end of the lead and a distal end of the lead; a proximal lead portion configured for attachment of the proximal end of the lead body to an electrical pulse generator; a distal portion, comprising a distal-most section comprising at least a first electrode, the distal-most section being configured and dimensioned to permit the first electrode to engage cardiac tissue within one of a patient's ventricle and patient's great cardiac vein to permit electrical stimulation thereof; an atrial section disposed proximally from the distal-most portion and comprising at least a second electrode, the atrial section comprising an elongated first proximal atrial portion having a first orientation defined by a first imaginary axis disposed along a first major axis thereof, an elongated second atrial pre-formed portion having a second length and having a second orientation defined by a second imaginary axis disposed along a second major axis thereof, an elongated third atrial pre-formed portion having a third length and having a third orientation defined by a third imaginary axis disposed along a third major axis thereof, an elongated fourth atrial pre-formed portion having a fourth length and having a fourth orientation defined by a fourth imaginary axis disposed along a fourth major axis thereof, and an elongated fifth distal atrial portion having a fifth orientation defined by a fifth imaginary axis disposed along a fifth major axis thereof, a first curve defined by an angle $\alpha_1$ between the first imaginary axis and the second imaginary axis, the first curve separating the first proximal atrial portion from the second atrial pre-formed portion, a second curve defined by an angle $\alpha_2$ between the second imaginary axis and the third imaginary axis, the second curve separating the second atrial pre-formed portion from the third atrial pre-formed portion, a third curve defined by an angle $\alpha'_2$ between the third imaginary axis and the fourth imaginary axis, the third curve separating the third atrial pre-formed portion from the fourth atrial pre-formed portion, a fourth curve defined by an angle $\alpha'_1$ between the fourth imaginary axis and the fifth imaginary axis, the fourth curve separating the fourth atrial pre-formed portion from the fifth distal atrial portion; wherein the angles $\alpha_1$, $\alpha_2$, $\alpha'_2$, and $\alpha'_1$ each range between about 90 degrees and about 135 degrees, the second length ranges between about 12 mm and about 35 mm, the third length ranges between about 12 mm and about 40 mm, and the fourth length ranges between about 12 mm and about 40 mm.

DETAILED DESCRIPTION OF THE PREFERRED EMBODIMENTS

Figure 1:
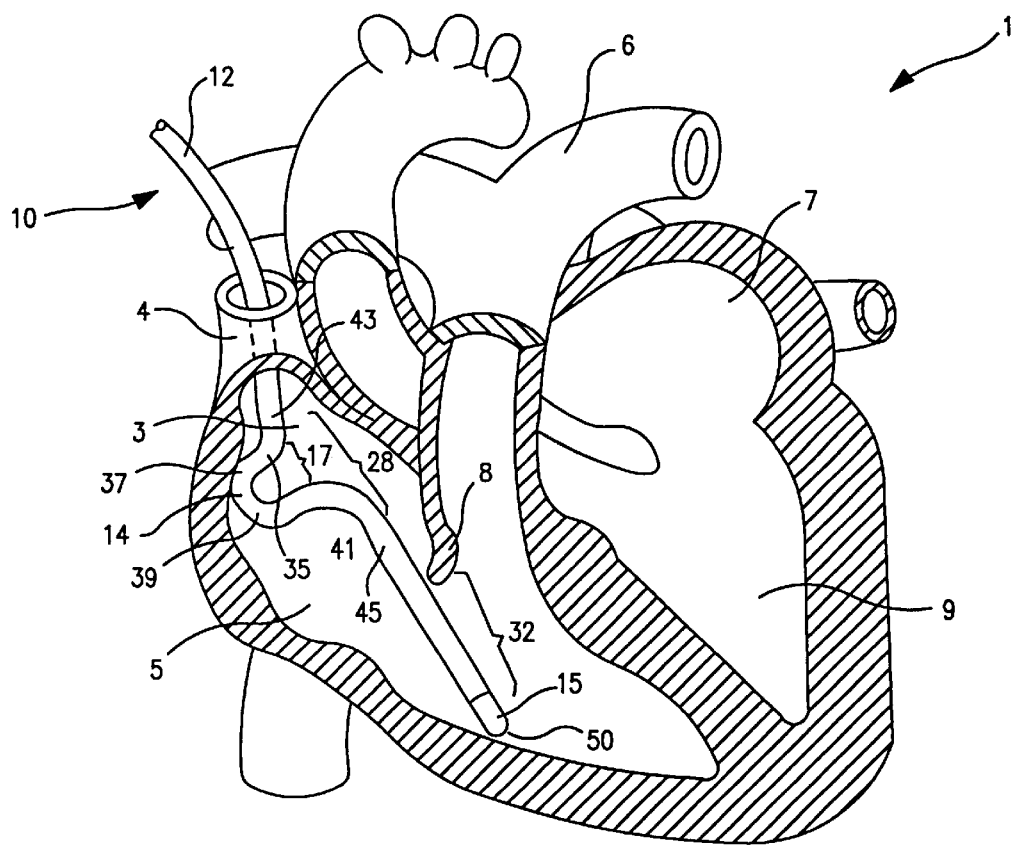
FIG. 1 shows a prior art single pass DDD lead implanted within the human heart.

FIG. 1 shows lead 10 of the prior art implanted within human heart 1. Atrial section 28 of lead 10 includes electrode 14 for stimulating the right atrial wall thereof, while ventricular electrode 15 of distal-most section 32 is disposed in right ventricle 5 for stimulation thereof. Owing to the variability and the morphology of human hearts, as well as the inherent positional and mechanical instability usually characterizing a medical electrical lead implanted within a human heart, atrial electrode 14 of lead 10 may or may not contact the right atrial wall of heart 1 sufficiently to stimulate same. This problem is exacerbated by the movement of the human heart when it beats, which typically causes the distal tip of a lead implanted in the ventricle to be pushed upwardly when the ventricle contracts. This, in turn, can cause the atrial electrodes to be pushed away from the atrial wall when the ventricle contracts, thereby leading to a loss of electrode coupling. It is one of the objects of the present invention to provide a solution to this problem. Note that in FIG. 1 curves 35, 37, 39 and 41 of U-shaped portion 17 of atrial section 28 of lead 10 are relatively gradual and not abrupt.

Figure 2:
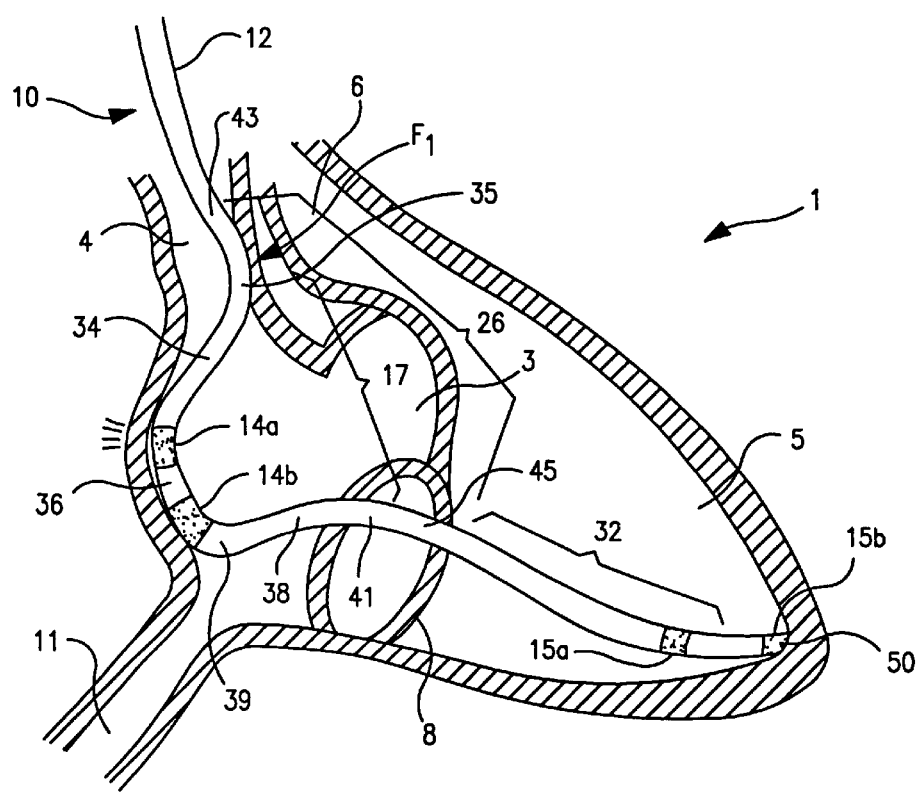
FIG. 2 shows a lead of the present invention implanted in the right atrium and the right ventricle.

FIG. 2 shows a cross-sectional representation of portions of human heart 1 within which one embodiment of lead 10 of the present invention is implanted. Single pass lead 10 shown in FIG. 2 is implanted in human heart 1 via superior vena cava 4 to enter right atrium 3 and right ventricle 5 after passing through tricuspid valve 8. Distal tip 50 of lead 10 is shown as being disposed at the apex of right ventricle 5. Stimulating electrodes 15(a) and 15(b) are disposed in distal-most section 32 of lead 10, and are intended to provide electrical stimulation of ventricular portions of heart 1. In right atrium 3, stimulating electrodes 14(a) and 14(b) are positioned against the right wall of atrium 3 owing to the unique geometric configuration of atrial section 28 of lead 10.

More particularly, atrial section 28 of lead 10 comprises the following pre-formed or pre-bent sections, each having pre-determined dimensions and orientations respecting one another: first atrial proximal portion 43, second atrial portion 34, third atrial portion 36, fourth atrial portion 38, and fifth atrial distal portion 45. U-shaped portion 17 of atrial section 28 comprises second atrial portion 34, third atrial portion 36, and fourth atrial portion 38. Portions of superior vena cava 4 push against portions of atrial proximal portion 43 such that third portion 36 is pushed against the right atrial wall to thereby provide good coupling between electrodes 14(a) and 14(b) and the right atrial wall. In other words, force $F_1$ in FIG. 2 is transmitted from first portion 43 through second portion 34 to third portion 36. Portions 34, 36 and 38 of atrial section 28 are appropriately dimensioned and configured to ensure good coupling of electrodes 14(a) and 14(b) against the right atrial wall, more about which we say below. Likewise, the distance between atrial section 28 and tip 50 is preferably optimized to cause third portion 36 to appropriately engage the right atrial wall. Note further that curves 37, 39 and 41 shown in FIGS. 2 through 4(a) are more abrupt and less gradual than those illustrated in the prior art lead of FIG. 1, and are characteristic of at least some embodiments of the present invention.

Figure 3:
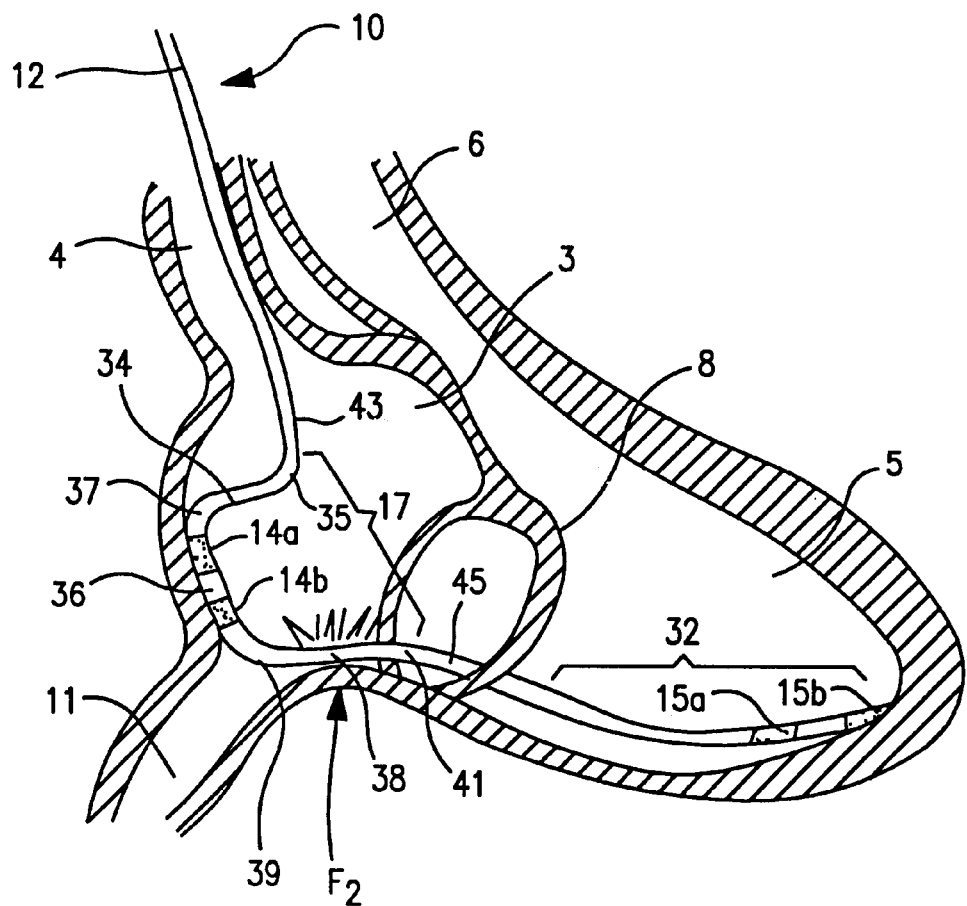
FIG. 3 shows another embodiment of the present invention implanted in the right atrium and the right ventricle.

Referring now to FIG. 3, there is shown lead 10 of FIG. 2 implanted within human heart 1 which differs dimensionally from heart 1 shown and illustrated in FIG. 2. In heart 1 of FIG. 3, atrium 3 is larger, resulting in lead 10 sitting lower within heart 1 of FIG. 3 than it does in heart 1 of FIG. 2. In one embodiment of the present invention, fourth portion 38 of atrial section 28 provides a gravity assist to lodge lead 10 within atrium 3 such that electrodes 14(a) and/or 14(b) appropriately engage right atrial wall 47. That is, once lead 10 has been pushed into right atrium 3 and right ventricle 5 such that distal tip 50 engages the apical portions of heart 1, and when heart 1 is relatively large, fourth atrial portion 38 may be configured and dimensioned such that portion 38 provides appropriate structural support to the maintain the proper positioning and emplacement of electrodes 14(a) and 14(b) against the walls of atrium 3 through means of fourth atrial portion 38 appropriately engaging regions of atrium 3 located near inferior vena cava 11 and/or heart valve 8.

In yet another embodiment of the present invention, a single pass lead is provided which is configured and dimensioned such that one or more atrial electrodes 14 thereof appropriately contact the right atrial wall and/or the coronary sinus wall when lead 10 is implanted in atrium 3, and where distal-most portion 32 thereof is configured to be positioned within the great cardiac vein or the coronary sinus to stimulate any one of the three remaining chambers of the heart, and where further only one lead body is employed to stimulate such a plurality of heart chambers.

Details concerning the construction and configuration of at least some embodiments of distal-most portion 32 of lead 10 of the present invention may be found in various publications, including U.S. Pat. No. 5,922,014 to Warman et al. for "Single pass lead and method of use"; U.S. Pat. No. 5,849,032 to van Venrooij for "Single pass medical electrical lead"; U.S. Pat. No. 5,628,778 to Kruse et al. for "Single pass medical electrical lead".

Figure 4A:
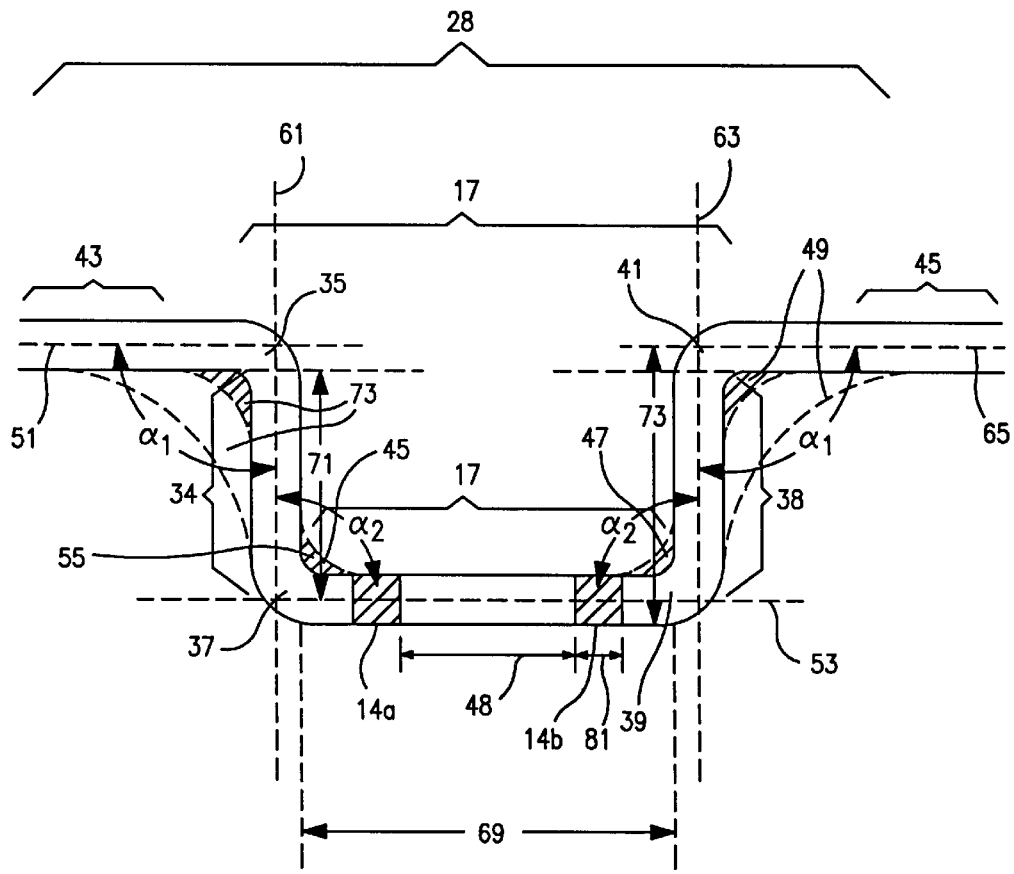
FIG. 4(a) shows one embodiment of an atrial section of a medical electrical lead of the present invention.

Referring now to FIG. 4(a), there is shown another embodiment of atrial section 28 of lead 10 of the present invention. Included and forming a portion of atrial section 28 is atrial proximal portion 43. Located distally from fourth atrial portion 38 of fifth atrial distal portion 45, which also forms a portion of atrial section 28. More particularly, atrial section 28 comprises first atrial proximal portion 43, first curve 35, second atrial pre-formed portion 34, second curve 37, third atrial pre-formed portion 36, third curve 39, fourth atrial pre-formed portion 38, fourth curve 41, and fifth atrial distal portion 45. First curve 35 separates atrial proximal portion 43 from first pre-formed portion 34. Similarly, fourth curve 41 separates fifth atrial distal portion 45 from fourth pre-formed portion 38. Second curve 37 separates second atrial portion 34 from third atrial portion 36, and third curve 39 separates third atrial portion 36 from fourth atrial portion 38.

The angle between first imaginary axis 51 of first atrial proximal portion 43 and second imaginary axis 61 of second atrial pre-formed portion 34 is defined by angle $\alpha_1$ shown in FIG. 4(a). Angle $\alpha'_1$ defines the angle between fourth imaginary axis 63 of fourth atrial portion 38 and fifth imaginary axis 65 of atrial distal portion 45 as shown in FIG. 4(a). Note that angle $\alpha_1$ in FIG. 4(a) between portions 43 and 34 may be different from angle $\alpha'_1$ between portions 38 and 45, according to the particular embodiment of the present invention at hand.

Angle $\alpha_2$ in FIG. 4(a) defines the relative orientations of second and third imaginary axes 61 and 53 of portions 34 and 36, respectively. Angle $\alpha_2$ defines the relative orientations of third and fourth imaginary axes 53 and 63 of portions 36 and 38, respectively. Note that angle $\alpha_2$ in FIG. 4(a) between the imaginary axes of portions 34 and 36 may be different from angle $\alpha'_2$ between the imaginary axes of portions 36 and 38, according to the particular embodiment of the present invention at hand.

Angles $\alpha_1$ and $\alpha'_1$ may range between about 90 degrees and 135 degrees, and may also be about 100 degrees, about 105 degrees, about 110 degrees, about 115 degrees, about 120 degrees, about 125 degrees and about 130 degrees.

Continuing to refer to FIG. 4(a), atrial section 28 is disposed proximally from distal-most portion 32 (not shown in FIG. 4(a)). A preferred embodiment of atrial section 28 comprises two electrodes 14(a) and 14(b). Alternatively, atrial section 28 may include only one electrode, or may comprise more than two electrodes.

Atrial section 28 comprises elongated first proximal atrial portion 43 having a first orientation defined by first imaginary axis 51 disposed along a first major axis thereof. Elongated second atrial pre-formed portion 34 has second length 71 and a second orientation defined by second imaginary axis 61 disposed along a second major axis thereof. Elongated third atrial pre-formed portion 36 has third length 69 and a third orientation defined by third imaginary axis 53 disposed along a third major axis thereof. Elongated fourth atrial pre-formed portion 38 has fourth length 73 and a fourth orientation defined by fourth imaginary axis 63 disposed along a fourth major axis thereof. Elongated fifth distal atrial portion 45 has a fifth orientation defined by fifth imaginary axis 65 disposed along a fifth major axis thereof.

In one embodiment of the present invention, third imaginary axis 53 of third atrial portion 36 may be substantially parallel to first imaginary axis 51 of first atrial portion 43. In another embodiment of the present invention, third imaginary axis 53 of third atrial portion 36 may be substantially parallel to fifth imaginary axis 65 of fifth atrial portion 45. In still another embodiment of the present invention, third imaginary axis 53 of third atrial portion 36 may be substantially parallel to both first imaginary axis 51 of first atrial portion 43 and fifth imaginary axis 65 of fifth atrial portion 45.

Angles $\alpha_1$, $\alpha_2$, $\alpha'_2$, and $\alpha'_1$ may each range between about 90 degrees and about 135 degree. Any of angles $\alpha_1$, $\alpha_2$, $\alpha'_2$, and $\alpha'_1$, may be selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

Second length 71 preferably ranges between about 12 mm and about 35 m, but may also be selected from the group consisting of about 12 mm, about 14 mm, about 16 mm, about 18 mm, about 20 mm, about 22 mm, about 24 mm, about 26 mm, about 28 mm, about 30 mm, about 32 mm, and about 35 mm.

Fourth length 73 preferably ranges between about 12 mm and about 35 m, but may also be selected from the group consisting of about 12 mm, about 14 mm, about 16 mm, about 18 mm, about 20 mm, about 22 mm, about 24 mm, about 26 mm, about 28 mm, about 30 mm, about 32 mm, and about 35 mm.

Third length 69 most preferably ranges between about 12 mm and about 40 mm, but may also be selected from the group consisting of about 12 mm, about 14 mm, about 16 mm, about 18 mm, about 20 mm, about 22 mm, about 24 mm, about 26 mm, about 28 mm, about 30 mm, about 32 mm, about 34 mm, about 36 mm, about 38 mm, and about 40 mm.

Atrial section 28 of the medical electrical lead of the present invention most preferably includes at least one electrode disposed on third atrial pre-formed portion 36. In a preferred embodiment of the present invention, third atrial portion 36 comprises two electrodes 14(a) and 14(b), which are most preferably separated by inter-electrode distance 48 greater than 8 mm, although other electrode separations are contemplated in the present invention.

For example, inter-electrode distance 48 most preferably ranges between about 4 mm and about 20 mm, but may also be selected from the group consisting of about 2 mm, about 3 mm, about 4 mm, about 5 mm, about 6 mm, about 7 mm, about 8 mm, about 8.5 mm, about 9 mm, about 10 mm, about 11 mm, about 12 mm, about 13 mm, about 14 mm, about 15 mm, about 16 mm, about 17 mm, about 18 mm, about 19 mm, and about 20 mm.

Width 81 of each of electrodes 14(a) and 14(b) along a direction parallel to imaginary axis 53 most preferably ranges between about 1 mm and about 2 mm, but may also be selected from the group consisting of about 0.25 mm, about 0.5 mm, about 0.75 mm, about 1 mm, about 1.25 mm, about 1.5 mm, about 1.75 mm, about 2 mm, about 2.5 mm, about 3 mm, and about 4 mm.

Figure 4B:
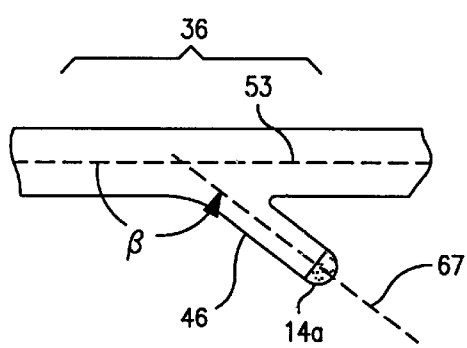
FIG. 4(b) shows one embodiment of an electrode configuration of the present invention.

In another embodiment of the present invention shown in FIG. 4(b), electrode 14(a) is attached to member 46 extending outwardly from third atrial pre-formed portion 36, member 46 having sixth imaginary axis 67 defining a major axis thereof. Sixth imaginary axis 67 is oriented at an angle β in respect of the third imaginary axis 53, angle β ranging between about 30 degrees and about 150 degrees. Angle β may be selected from the group consisting of about 30 degrees, about 40 degrees, about 50 degrees, about 60 degrees, about 70 degrees, about 80 degrees, about 90 degrees, about 100 degrees, about 110 degrees, about 120 degrees, about 130 degrees, about 140 degrees, and about 150 degrees.

Figure 6:
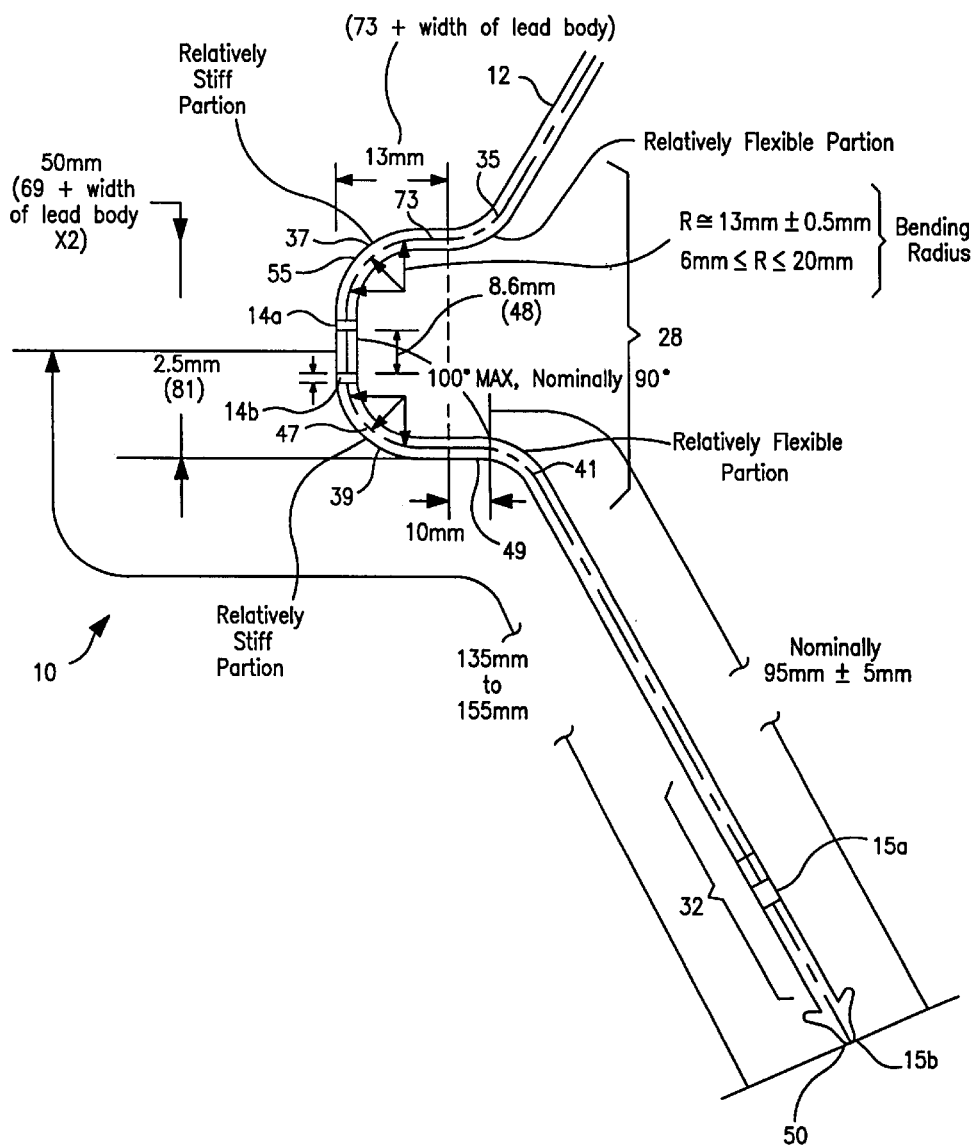
FIG. 6 shows preferred dimensions and other details concerning the embodiment of the invention illustrated in FIG. 5.

Moreover, and as shown in FIG. 6, second, third and fourth atrial portions 34, 36 and 38, respectively, may be separated by second and third curves 37 and 39, respectively, wherein either or both of curves 37 and 39 may be characterized in having a bend radius R selected from the group consisting of about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm. As shown in FIG. 6, a nominal bend radius R is 13 mm, plus or minus 0.5 mm.

Note further that the use of electrode configurations other than those shown explicitly in the Figures are contemplated in the present invention. Likewise, affixation devices not shown explicitly in the Figures such as screws, hooks, barbs, tines and the like are also contemplated in the present invention.

As shown in FIG. 4(a), atrial section 28 may be provided with optional structural reinforcement members 73, 55, 47 and 49, such members most preferably being formed of a suitable biostable, biocompatible material such as silicon, polyurethane, polyethylene, and/or silastic. Atrial section 28 and distal-most section 32 may also be characterized in exhibiting variations in bending stiffness to aid in retaining lead 10 within heart 1 such that the electrodes are remain suitably coupled to their respective portions of heart 1 following implantation.

In yet another embodiment of the present invention, first, second, third, fourth and fifth atrial portions 43, 34, 36, 38 and 45, respectively, are configured and dimensioned so as to urge electrode 14(a) and/or 14(b) against an atrial wall of patient's heart 1 when atrial section 23 is implanted within the atrium. In another embodiment of the present invention, first, second, third, fourth and fifth atrial portions 43, 34, 36, 38 and 45, respectively, are configured and dimensioned so as to urge at least one electrode against a right coronary sinus atrial wall of the patient's heart when atrial section 28 of lead 10 is implanted within the patient's right atrium.

In still another embodiment of the present invention, fourth atrial portion 38 is configured and dimensioned such that fourth atrial portion 38 engages at least one of a first region of the patient's heart located near an inferior vena cava and a second region of the patient's heart located near tricuspid heart valve 8.

In other embodiments of the present invention, atrial section 28 and distal-most section 32 are configured and dimensioned to permit atrial section 28 to be implanted within right atrium 3 and distal-most section 32 to be implanted within a great cardiac vein or a coronary sinus of the patient's heart.

In some embodiments of the present invention, atrial portion 28 of lead 10 is substantially similar to that shown in FIGS. 2, 3 and 4 hereof, but distal portion 32 of lead 10 is disposed in the great cardiac vein or coronary sinus via the ostium. Such an embodiment of the present invention permits stimulation of the right atrium as well as of the left atrium and/or left ventricle, depending upon the particular position of electrodes located on distal portion 32 of lead 10. That is, atrial portion 28 of the present invention many be employed in conjunction with single pass leads designed to stimulate the left atrium and the left ventricle. Details concerning the construction and configuration of such a distal portion 32 of lead 10 of the present invention may be found in U.S. patent appln. Ser. No. 08/980,438 to Hine et al. for "Medical electrical lead", the disclosure of which is hereby incorporated by reference herein in its entirety.

Figure 5:
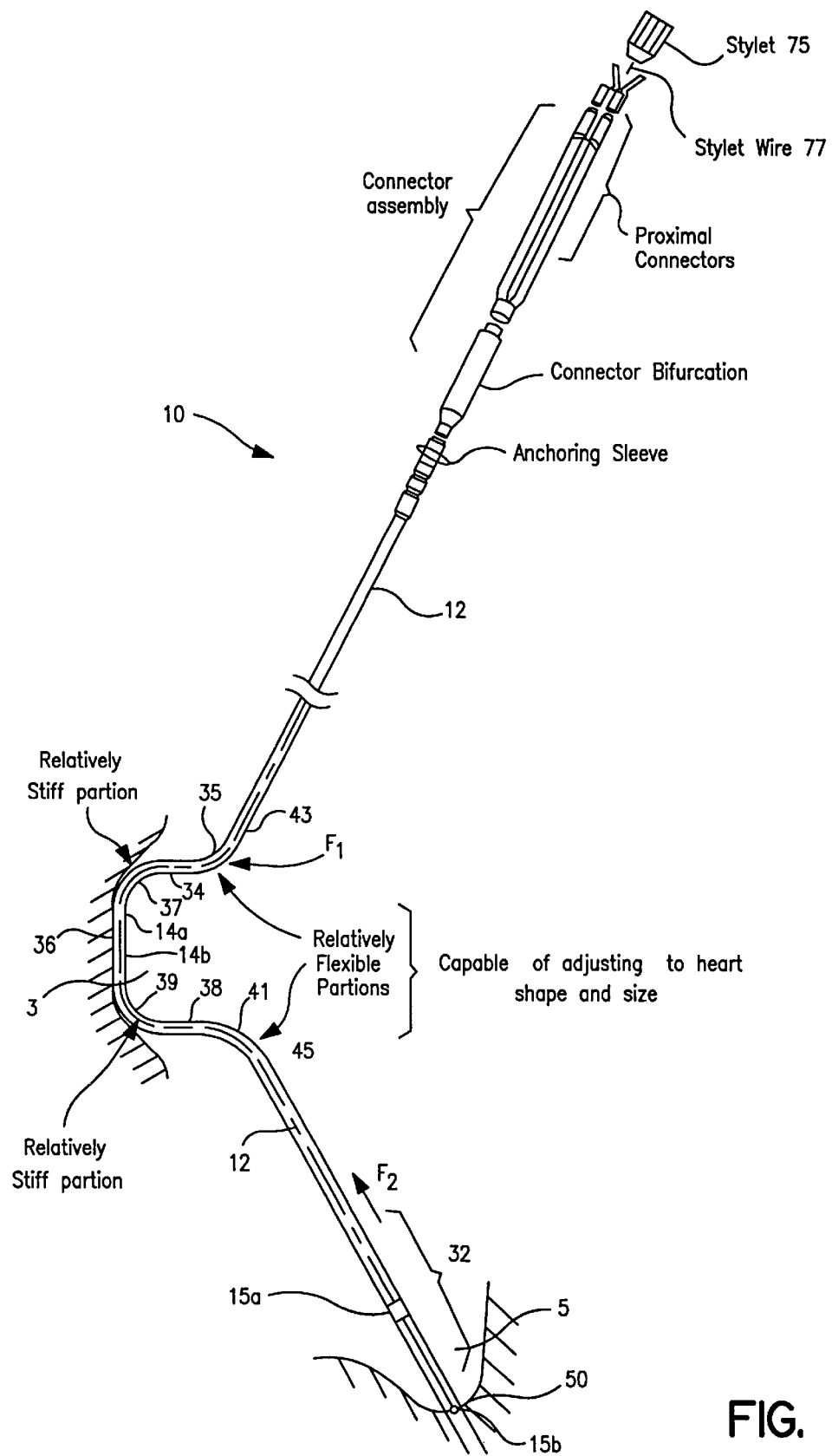
FIG. 5 shows another embodiment of the present invention.

In another embodiment of the present invention illustrated in FIG. 5, lead 10 has an internal lumen disposed therewithin along at least a substantial portion of a length of the lead, the lumen being configured and dimensioned to accept straightening stylet wire 77 therewithin to aid in the lead implantation process. Stylet wire 77 may be employed to straighten lead 10 for implantation. Once stylet wire 77 is withdrawn the lead body assumes its predetermined shape. Implantation of the lead of the present invention may occur in a manner such as that described in columns 7 and 8 of U.S. Pat. No. 5,628,778 to Kruse et al. for "Single Pass Medical Electrical Lead", the disclosure of which is hereby incorporated by reference herein in its entirety.

Alternatively, lead 10 may be configured and dimensioned for implantation in cooperation with a guiding catheter configured to accept the lead therewithin and guide the lead to a predetermined site within the patient's heart. Such a guide catheter may be formed, for example, from PEBAX (polyether block amide) available from Adochem Corporation of Massachusetts. PEBAX is a preferred material for many guide catheters because of its kink resistance, durability, good shear resistance characteristics, and because it is available in a range of hardnesses.

Continuing to refer to FIG. 5, there is shown a preferred embodiment of medical electrical lead 10 of the present invention. Relatively stiff portions are located near bends 37 and 39 of atrial section 28, while relatively flexible portions are disposed near bends 41 and 35 of atrial section 28. In the embodiment of the present invention illustrated in FIG. 5, relative stiffness are imparted to portions 34, 36 and 38 of atrial section 28 by structurally reinforcing or thickening such portions of atrial section 28 in respect of atrial sections 43 and 45. Tip 50 of ventricular section 32 exerts upward force $F_2$ on lead body 12. Substantially lateral force $F_1$ is likewise exerted near bend 35 of atrial section 28. Forces $F_1$ and $F_2$ act to push atrial electrodes 14(a) and 14(b) against the wall of atrium 3. Relatively flexible portions of atrial section 28 located at or near bends 35 and 41 of atrial section 28 are most preferably sufficiently flexible to be capable of adjusting to individual heart sizes and shapes.

Referring now to FIG. 6, there are shown preferred dimensions and other details concerning the embodiment of the invention illustrated in FIG. 5. Preferred dimensions 73, 69, 81, 48, as well as dimensions respecting the length of lead 10 from atrial section 28 to tip 50, as well as the length of lead 10 from tip 50 to a location midway between electrodes 14(a) and 14(b).

Also shown in FIG. 6 is bend radius R defining the curvature of bends 37 and 39. As shown in FIG. 6, preferred bending radius is 13 mm, plus or minus 0.5 mm. Bending radius R may vary between about 6 mm and about 20 mm, however, and may further be selected from the group consisting of about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, and about 20 mm.

Referring now to FIGS. 2 through 4(b), the distinctive U-shape construction of the lead of the present invention may be achieved using different manufacturing processes. It is preferred that portion 36 of lead 10 and corresponding imaginary axis 53 remain parallel to portions 43 and 45 and corresponding axes 51 and 65 thereof. Inter-electrode distance 48 is most preferably at least 8 mm.

In preferred embodiments of the present invention, distance 69 most preferably ranges between about 20 mm and about 25 mm, distance 69 most preferably being determined by the structures present in the right heart. In the present invention, it is preferred that section 36 of lead 10 lodge between tissue structures disposed on the wall of right atrium 3 but perpendicular to the plane of valve 8.

In preferred embodiments of the present invention, distance 71 is optimally about 20 mm in length. Distance 71 and the stiffness imparted to lead body 12 in and around curves 35 and 41 determine the force with which portion 36 is pressed against the wall of the heart. As discussed above, bending stiffness of various portions of lead body 12 may be varied through various means such as optional silicone reinforcements 73 and 49 discussed hereinabove, or by employing the teachings of U.S. Pat. No. 5,800,497 to Bakels et al. for "Medical Electrical Lead With Temporary Stiff Portion"

Not shown in the Figures are electrical conductors disposed within lead body 12 which transmit electrical stimulation signals provided by an implantable pulse generator (IPG) such as a pacemaker, implantable cardio-defibrillator (ICD), pacer-cardio-defibrillator (PCD) or the like to electrodes disposed on the atrial and distal-most sections of the distal portion of the lead. Most preferably, such electrical conductors comprise strands of twisted, wound or braided stainless steel wire, and are capable of reliably conducting electrical current after having been subjected to numerous, repeated bending and torquing stresses. Wires formed from materials other than stainless steel may be employed to form such conductors, such as nickel-titanium alloys such as NITINOL™, platinum, gold, silver, palladium, other noble metals, and other alloys or metals suitable for use in the human body.

Such conductors are mechanically and electrically connected to connectors disposed on the proximal end of lead 10, and permit the attachment thereof to the implantable pulse generator. It is preferred that the DC resistance of the conductors employed in lead 10 not exceed about 50 Ohms per meter for the combined total resistance of the strands or wires forming each conductor.

Also not shown in the Figures is an electrically insulative layer which separates and electrically insulates the conductors from one another within lead body 12. Such a layer is preferably formed of a fluoro-copolymer such as fluorinated ethylene propylene (FEP) or TEFLON 100™, but may also be formed of nylon or any other suitable material. FEP is a preferred insulation material because of the low shrink ratio it exhibits upon being subjected to heat.

Portions of lead body 12 may be formed from a suitable biocompatible material such as a polyurethane, a polyethylene, silastic compounds, combinations or mixtures of the foregoing, or any other suitable biostable, biocompatible substance capable of withstanding the corrosive effects presented by human or mammalian body fluids.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to pacing leads for bradycardia applications per se, but may find further application as a cardiac sensing lead only, a fetal monitoring and sensing lead, a defibrillating lead, a fluoroless lead, a balloon lead, or a lead for use in stent implantation or other surgical procedure where cardiac backup or pacing support is required.

The present invention includes within its scope methods of implanting, using and making the leads described hereinabove.

All printed publications referenced hereinabove, including all patents and patent applications, are hereby incorporated by reference into the specification hereof, each in its respective entirety.

As those skilled in the art will appreciate readily upon reading the Summary of the Invention, the Detailed Description of the Preferred Embodiments and the Claims set forth below, at least some of the devices and methods disclosed in the patents referenced herein may be modified advantageously in accordance with the teachings of the present invention.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. An elongated medical electrical lead for intra-cardiac electrical stimulation of a heart of a patient, comprising:
   (a) a lead body extending between a proximal end of the lead and a distal end of the lead;
   (b) a proximal lead portion configured for attachment of the proximal end of the lead body to an electrical pulse generator;
   (c) a distal portion, comprising:
      (i) a distal-most section comprising at least a first electrode, the distal-most section being configured and dimensioned to permit the first electrode to engage cardiac tissue within one of a patient's ventricle and patient's great cardiac vein to permit electrical stimulation thereof;
      (ii) an atrial section disposed proximally from the distal-most portion and comprising at least a second electrode, the atrial section comprising an elongated first proximal atrial portion having a first orientation defined by a first imaginary axis disposed along a first major axis thereof, an elongated second atrial pre-formed portion having a second length and having a second orientation defined by a second imaginary axis disposed along a second major axis thereof, an elongated third atrial pre-formed portion having a third length and having a third orientation defined by a third imaginary axis disposed along a third major axis thereof, an elongated fourth atrial pre-formed portion having a fourth length and having a fourth orientation defined by a fourth imaginary axis disposed along a fourth major axis thereof, and an elongated fifth distal atrial portion having a fifth orientation defined by a fifth imaginary axis disposed along a fifth major axis thereof, a first curve defined by an angle $\alpha_1$ between the first imaginary axis and the second imaginary axis, the first curve separating the first proximal atrial portion from the second atrial pre-formed portion, a second curve defined by an angle $\alpha_2$ between the second imaginary axis and the third imaginary axis, the second curve separating the second atrial pre-formed portion from the third atrial pre-formed portion, a third curve defined by an angle $\alpha'_2$ between the third imaginary axis and the fourth imaginary axis, the third curve separating the third atrial pre-formed portion from the fourth atrial pre-formed portion, a fourth curve defined by an angle $\alpha'_1$ between the fourth imaginary axis and the fifth imaginary axis, the fourth curve separating the fourth atrial pre-formed portion from the fifth distal atrial portion;

wherein the angles $\alpha_1$, $\alpha_2$, $\alpha'_2$, and $\alpha'_1$ each range between about 90 degrees and about 135 degrees, the second length ranges between about 12 mm and about 35 mm, the third length ranges between about 12 mm and about 40 mm, and the fourth length ranges between about 12 mm and about 40 mm.

2. The medical electrical lead of claim 1, wherein the angle $\alpha_2$ is selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

3. The medical electrical lead of claim 1, wherein the angle $\alpha_2$ is selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

4. The medical electrical lead of claim 1, wherein the angle $\alpha'_1$ is selected from the group consisting of about 90 degrees, about 95 degrees, about 100 degrees, about 125 degrees, about 110 degrees, about 115 degrees, about 120 degrees, about 125 degrees, about 130 degrees and about 135 degrees.

5. The medical electrical lead of claim 1, wherein the angle $\alpha'_2$ is selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

6. The medical electrical lead of claim 1, wherein the second length is selected from the group consisting of about 12 mm, about 14 mm, about 16 mm, about 18 mm, about 20 mm, about 22 mm, about 24 mm, about 26 mm, about 28 mm, about 30 mm, about 32 mm, and about 35 mm.

7. The medical electrical lead of claim 1, wherein the fourth length is selected from the group consisting of about 12 mm, about 14 mm, about 16 mm, about 18 mm, about 20 mm, about 22 mm, about 24 mm, about 26 mm, about 28 mm, about 30 mm, about 32 mm, and about 35 mm.

8. The medical electrical lead of claim 1, wherein the third length is selected from the group consisting of about 12 mm, about 14 mm, about 16 mm, about 18 mm, about 20 mm, about 22 mm, about 24 mm, about 26 mm, about 28 mm, about 30 mm, about 32 mm, about 34 mm, about 36 mm, about 38 mm, and about 40 mm.

9. The medical electrical lead of claim 1, wherein the second electrode is disposed on the third atrial pre-formed portion.

10. The medical electrical lead of claim 1, wherein the second electrode is attached to a member extending outwardly from the third atrial pre-formed portion, the member having a sixth imaginary axis defining a major axis thereof.

11. The medical electrical lead of claim 10, wherein the sixth imaginary axis is oriented at an angle $\beta$ in respect of the third imaginary axis, the angle $\beta$ ranging between about 30 degrees and about 150 degrees.

12. The medical electrical lead of claim 11, wherein the angle $\beta$ is selected from the group consisting of about 30 degrees, about 40 degrees, about 50 degrees, about 60 degrees, about 70 degrees, about 80 degrees, about 90 degrees, about 100 degrees, about 110 degrees, about 120 degrees, about 130 degrees, about 140 degrees, and about 150 degrees.

13. The medical electrical lead of claim 1, wherein the second electrode is disposed on the third atrial pre-formed portion along with a third electrode, the second and third electrodes being separated by an inter-electrode distance.

14. The medical electrical lead of claim 13, wherein the inter-electrode distance ranges between about 4 mm and about 20 mm.

15. The medical electrical lead of claim 13, wherein the inter-electrode distance is selected from the group consisting of about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, and about 20 mm.

16. The medical electrical lead of claim 1, wherein the second electrode has a width ranging between about 1 mm and about 2 mm.

17. The medical electrical lead of claim 1, wherein the second electrode has a width selected from the group consisting of about 0.25 mm, about 0.5 mm, about 0.75 mm, about 1 mm, about 1.25 mm, about 1.5 mm, about 1.75 mm, about 2 mm, about 2.5 mm, about 3 mm, and about 4 mm.

18. The medical electrical lead of claim 1, wherein the third imaginary axis of the third atrial portion is substantially parallel to the first imaginary axis of the first atrial portion.

19. The medical electrical lead of claim 1, wherein the third imaginary axis of the third atrial portion is substantially parallel to the fifth imaginary axis of the fifth atrial portion.

20. The medical electrical lead of claim 1, wherein at least one reinforcement member is disposed in the region of the at least one of the first curve, the second curve and the third curve.

21. The medical electrical lead of claim 20, wherein the at least one reinforcement member comprises a material selected from the group consisting of silicone, silastic, polyurethane, urethane, rubber, silicone rubber, and polyethylene.

22. The medical electrical lead of claim 1, wherein distal portion of the lead is further characterized in exhibiting variations in bending stiffness.

23. The medical electrical lead of claim 1, wherein the lead further has an internal lumen disposed therewithin along at least a substantial portion of a length of the lead, the lumen being configured and dimensioned to accept a stylet therewithin.

24. The medical electrical lead of claim 1, wherein the lead further comprises a guiding catheter configured to accept the lead therewithin and guide the lead to a predetermined site within the patient's heart.

25. The medical electrical lead of claim 1, wherein the first, second, third, fourth and fifth atrial portions are configured and dimensioned so as to urge at least the second electrode against an atrial wall of the patient's heart when implanted within an atrium of the patient's heart.

26. The medical electrical lead of claim 1, wherein the second, third and fourth atrial portions are configured and dimensioned so as to urge at least the second electrode against a right coronary sinus atrial wall of the patient's heart when the atrial portion of the lead is implanted within an atrium of the patient's heart.

27. The medical electrical lead of claim 1, wherein the fourth atrial portion is configured and dimensioned such that the fourth atrial portion engages at least one of a first region of the patient's heart located near an inferior vena cava and a second region of the patient's heart located near a tricuspid heart valve.

28. The medical electrical lead of claim 1, wherein the second, third and fourth atrial portions are configured and dimensioned such that the fourth atrial portion engages at least one of a first region of the patient's heart located near an inferior vena cava and a second region of the patient's heart located near a tricuspid heart valve.

29. The medical electrical lead of claim 1, wherein the atrial section and the distal-most section are configured and dimensioned to permit the atrial section to be implanted within a right atrium of the patient's heart and the distal-most section to be implanted within a right ventricle of the patient's heart.

30. The medical electrical lead of claim 1, wherein the atrial section and the distal-most section are configured and dimensioned to permit the atrial section to be implanted within a right atrium of the patient's heart and the distal-most section to be implanted within a great cardiac vein of the patient's heart.

31. The medical electrical lead of claim 1, wherein the atrial section and the distal-most section are configured and dimensioned to permit the atrial section to be implanted within a right atrium of the patient's heart and the distal-most section to be implanted a coronary sinus of the patient's heart.

32. The medical electrical lead of claim 1, wherein the second curve has a bending radius selected from the group consisting of about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm.

33. The medical electrical lead of claim 1, wherein the third curve has a bending radius selected from the group consisting of about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm.

34. An elongated medical electrical lead for intra-cardiac electrical stimulation of a heart of a patient, comprising:
   (a) a lead body extending between a proximal end of the lead and a distal end of the lead;
   (b) a proximal lead portion configured for attachment of the proximal end of the lead body to an electrical pulse generator;
   (c) a distal portion, comprising:
      (i) a distal-most section comprising at least a first means for providing electrical stimulation to cardiac tissue, the distal-most section being configured and dimensioned to permit the first stimulating means to engage cardiac tissue within one of a patient's ventricle and patient's great cardiac vein to permit electrical stimulation thereof;
      (ii) an atrial section disposed proximally from the distal-most portion and comprising at least a second means for providing electrical stimulation to cardiac tissue, the atrial section comprising an elongated first proximal atrial portion having a first orientation defined by a first imaginary axis disposed along a first major axis thereof, an elongated second atrial pre-formed portion having a second length and having a second orientation defined by a second imaginary axis disposed along a second major axis thereof, an elongated third atrial pre-formed portion having a third length and having a third orientation defined by a third imaginary axis disposed along a third major axis thereof, an elongated fourth atrial pre-formed portion having a fourth length and having a fourth orientation defined by a fourth imaginary axis disposed along a fourth major axis thereof, and an elongated fifth distal atrial portion having a fifth orientation defined by a fifth imaginary axis disposed along a fifth major axis thereof, a first curve defined by an angle $\alpha_1$ between the first imaginary axis and the second imaginary axis, the first curve separating the first proximal atrial portion from the second atrial pre-formed portion, a second curve defined by an angle $\alpha_2$ between the second imaginary axis and the third imaginary axis, the second curve separating the second atrial pre-formed portion from the third atrial pre-formed portion, a third curve defined by an angle $\alpha'_2$ between the third imaginary axis and the fourth imaginary axis, the third curve separating the third atrial pre-formed portion from the fourth atrial pre-formed portion, a fourth curve defined by an angle $\alpha'_1$ between the fourth imaginary axis and the fifth imaginary axis, the fourth curve separating the fourth atrial pre-formed portion from the fifth distal atrial portion;
      wherein the angles $\alpha_1$, $\alpha_2$, $\alpha'_2$, and $\alpha'_1$ each range between about 90 degrees and about 135 degrees, the second length ranges between about 12 mm and about 35 mm, the third length ranges between about 12 mm and about 40 mm, and the fourth length ranges between about 12 mm and about 40 mm.

35. The medical electrical lead of claim 34, wherein the angle $\alpha_1$ is selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

36. The medical electrical lead of claim 34, wherein the angle $\alpha_2$ is selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

37. The medical electrical lead of claim 34, wherein the angle $\alpha'_1$ is selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

38. The medical electrical lead of claim 34, wherein the angle $\alpha'_2$ is selected from the group consisting of about 90 degrees, about 95 degrees, about 100 degrees, about 105 degrees, about 110 degrees, about 115 degrees, about 120 degrees, about 125 degrees, about 130 degrees and about 135 degrees.

39. The medical electrical lead of claim 34, wherein the second length is selected from the group consisting of about 12 mm, about 14 mm, about 16 mm, about 18 mm, about 20 mm, about 22 mm, about 24 mm, about 26 mm, about 28 mm, about 30 mm, about 32 mm, and about 35 mm.

40. The medical electrical lead of claim 34, wherein the fourth length is selected from the group consisting of about 12 mm, about 14 mm, about 16 mm, about 18 mm, about 20 mm, about 22 mm, about 24 mm, about 26 mm, about 28 mm, about 30 mm, about 32 mm, and about 35 mm.

41. The medical electrical lead of claim 34, wherein the third length is selected from the group consisting of about 12 mm, about 14 mm, about 16 mm, about 18 mm, about 20 mm, about 22 mm, about 24 mm, about 26 mm, about 28 mm, about 30 mm, about 32 mm, about 34 mm, about 36 mm, about 38 mm, and about 40 mm.

42. The medical electrical lead of claim 34, wherein the second electrode is disposed on the third atrial pre-formed portion.

43. The medical electrical lead of claim 34, wherein the first, second, third, fourth and fifth atrial portions are configured and dimensioned so as to urge at least the second electrode against an atrial wall of the patient's heart when implanted within an atrium of the patient's heart.

44. The medical electrical lead of claim 34, wherein the second, third and fourth atrial portions are configured and dimensioned so as to urge at least the second electrode against a right coronary sinus atrial wall of the patient's heart when the atrial portion of the lead is implanted within an atrium of the patient's heart.

45. The medical electrical lead of claim 34, wherein the fourth atrial portion is configured and dimensioned such that the fourth atrial portion engages at least one of a first region of the patient's heart located near an inferior vena cava and a second region of the patient's heart located near a tricuspid heart valve.

46. The medical electrical lead of claim 34, wherein the second, third and fourth atrial portions are configured and dimensioned such that the fourth atrial portion engages at least one of a first region of the patient's heart located near an inferior vena cava and a second region of the patient's heart located near a tricuspid heart valve.

47. The medical electrical lead of claim 34, wherein the atrial section and the distal-most section are configured and dimensioned to permit the atrial section to be implanted within a right atrium of the patient's heart and the distal-most section to be implanted within a right ventricle of the patient's heart.

48. The medical electrical lead of claim 34, wherein the atrial section and the distal-most section are configured and dimensioned to permit the atrial section to be implanted within a right atrium of the patient's heart and the distal-most section to be implanted within a great cardiac vein of the patient's heart.

49. The medical electrical lead of claim 34, wherein the atrial section and the distal-most section are configured and dimensioned to permit the atrial section to be implanted within a right atrium of the patient's heart and the distal-most section to be implanted a coronary sinus of the patient's heart.

50. The medical electrical lead of claim 34, wherein the second curve has a bending radius selected from the group consisting of about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm.

51. The medical electrical lead of claim 34, wherein the third curve has a bending radius selected from the group consisting of about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm.

52. A method of making an elongated medical electrical lead for intra-cardiac electrical stimulation of a heart of a patient, where the lead comprises a lead body extending between a proximal end of the lead and a distal end of the lead, a proximal lead portion configured for attachment of the proximal end of the lead body to an electrical pulse generator, a distal portion comprising a distal-most section comprising at least a first electrode, the distal-most section being configured and dimensioned to permit the first electrode to engage cardiac tissue within one of a patient's ventricle and patient's great cardiac vein to permit electrical stimulation thereof, an atrial section disposed proximally from the distal-most portion and comprising at least a second electrode, the atrial section comprising an elongated first proximal atrial portion having a first orientation defined by a first imaginary axis disposed along a first major axis thereof, an elongated second atrial pre-formed portion having a second length and having a second orientation defined by a second imaginary axis disposed along a second major axis thereof, an elongated third atrial pre-formed portion having a third length and having a third orientation defined by a third imaginary axis disposed along a third major axis thereof, an elongated fourth atrial pre-formed portion having a fourth length and having a fourth orientation defined by a fourth imaginary axis disposed along a fourth major axis thereof, and an elongated fifth distal atrial portion having a fifth orientation defined by a fifth imaginary axis disposed along a fifth major axis thereof, a first curve defined by an angle $\alpha'_1$ between the first imaginary axis and the second imaginary axis, the first curve separating the first proximal atrial portion from the second atrial pre-formed portion, a second curve defined by an angle $\alpha_2$ between the second imaginary axis and the third imaginary axis, the second curve separating the second atrial pre-formed portion from the third atrial pre-formed portion, a third curve defined by an angle $\alpha'_2$ between the third imaginary axis and the fourth imaginary axis, the third curve separating the third atrial pre-formed portion from the fourth atrial pre-formed portion, a fourth curve defined by an angle $\alpha'_1$ between the fourth imaginary axis and the fifth imaginary axis, the fourth curve separating the fourth atrial pre-formed portion from the fifth distal atrial portion, wherein the angles $\alpha_1$, $\alpha_2$, $\alpha'_2$, and $\alpha'_1$ each range between about 90 degrees and about 135 degrees, the second length ranges between about 12 mm and about 35 mm, the third length ranges between about 12 mm and about 40 mm, and the fourth length ranges between about 12 mm and about 40 mm, comprising:

(a) forming the distal-most section, and (b) forming the atrial section.

53. A method of implanting an elongated medical electrical lead for intra-cardiac electrical stimulation of a heart of a patient, where the lead comprises a lead body extending between a proximal end of the lead and a distal end of the lead, a proximal lead portion configured for attachment of the proximal end of the lead body to an electrical pulse generator, a distal portion comprising a distal-most section comprising at least a first electrode, the distal-most section being configured and dimensioned to permit the first electrode to engage cardiac tissue within one of a patient's ventricle and patient's great cardiac vein to permit electrical stimulation thereof, an atrial section disposed proximally from the distal-most portion and comprising at least a second electrode, the atrial section comprising an elongated first proximal atrial portion having a first orientation defined by a first imaginary axis disposed along a first major axis thereof, an elongated second atrial pre-formed portion having a second length and having a second orientation defined by a second imaginary axis disposed along a second major axis thereof, an elongated third atrial pre-formed portion having a third length and having a third orientation defined by a third imaginary axis disposed along a third major axis thereof, an elongated fourth atrial pre-formed portion having a fourth length and having a fourth orientation defined by a fourth imaginary axis disposed along a fourth major axis thereof, and an elongated fifth distal atrial portion having a fifth orientation defined by a fifth imaginary axis disposed along a fifth major axis thereof, a first curve defined by an angle $\alpha_1$ between the first imaginary axis and the second imaginary axis, the first curve separating the first proximal atrial portion from the second atrial pre-formed portion, a second curve defined by an angle $\alpha_2$ between the second imaginary axis and the third imaginary axis, the second curve separating the second atrial pre-formed portion from the third atrial pre-formed portion, a third curve defined by an angle $\alpha'_2$ between the third imaginary axis and the fourth imaginary axis, the third curve separating the third atrial pre-formed portion from the fourth atrial pre-formed portion, a fourth curve defined by an angle $\alpha'_1$ between the fourth imaginary axis and the fifth imaginary axis, the fourth curve separating the fourth atrial pre-formed portion from the fifth distal atrial portion, wherein the angles $\alpha_1$, $\alpha_2$, $\alpha'_2$, and $\alpha'_1$ each range between about 90 degrees and about 135 degrees, the second length ranges between about 12 mm and about 35 mm, the third length ranges between about 12 mm and about 40 mm, and the fourth length ranges between about 12 mm and about 40 mm, comprising:

(a) guiding the distal-most section through a blood vessel in the patient towards the patient's heart;

(b) implanting the distal-most section of the lead in one of a right ventricle of the patient's heart, a coronary sinus of the patient's heart, and a great cardiac vein of the patient's heart; and (c) implanting the atrial section of the lead in a right atrium of the patient's heart.

* * * * *

UNITED STATES PATENT AND TRADEMARK OFFICE
CERTIFICATE OF CORRECTION

PATENT NO.    : 6,301,507 B1
DATED         : October 9, 2001
INVENTOR(S)   : Bakels et al.

It is certified that error appears in the above-identified patent and that said Letters Patent is hereby corrected as shown below:

<u>Column 16,</u>
Line 37, change "angle $\alpha'_1$" to -- angle $\alpha_1$ --.

<u>Column 11,</u>
Line 44, change "about 125" to -- about 105 --.

<u>Column 14,</u>
Line 55, change "$\alpha'_2$" to -- $\alpha_2$ --.

Signed and Sealed this

Seventeenth Day of June, 2003

JAMES E. ROGAN
*Director of the United States Patent and Trademark Office*